United States Patent [19]

Rosenbrook et al.

[11] Patent Number: 4,613,589

[45] Date of Patent: Sep. 23, 1986

[54] D-MANNO-2-OCTULOSONIC ACID DERIVATIVES, PHARMACEUTICAL COMPOSITIONS AND METHOD OF USE

[75] Inventors: William Rosenbrook, Libertyville; Paul A. Lartey; David A. Riley, both of Waukegan, all of Ill.

[73] Assignee: Abbott Laboratories, North Chicago, Ill.

[21] Appl. No.: 767,212

[22] Filed: Aug. 19, 1985

[51] Int. Cl.$^4$ ............................ A61K 31/70; C07H 3/08
[52] U.S. Cl. ........................................ 514/23; 536/1.1; 536/18.7; 536/53; 536/55
[58] Field of Search ................... 514/23; 536/1.1, 18.2, 536/18.7, 17.2, 53, 55, 4.1

[56] References Cited

U.S. PATENT DOCUMENTS 3,719,659  3/1973  Magerlein ........................... 536/18.2
4,454,123  6/1984  Noyori et al. ......................... 514/23

OTHER PUBLICATIONS

Charon et al., "J.C.S." Perkin I, pp. 1971–1977, 1980.
Collins et al., "J.C.S. Chem. Comm.", pp. 1139–1140, 1981.
Strain et al., "J. Bio. Chem.", vol. 258, No. 22, pp. 13466–13477, 1983.
Strain et al., "J. Bio. Chem.", vol. 258, No. 5, pp. 2906–2910, 1983.
Bigham et al., "J. Med. Chem.", vol. 27, pp. 717–726, 1984.
Molin et al., "Tetrahedron Letters", vol. 26, No. 5, pp. 677–680, 1985.

*Primary Examiner*—Johnnie R. Brown
*Attorney, Agent, or Firm*—Steven F. Weinstock; Martin L. Katz

[57] ABSTRACT

Derivatives of 3-deoxy-D-manno-2-octulosonic acid (KDO) are potent inhibitors of bacterial enzymes and a novel class of antibacterial agents.

4 Claims, No Drawings

D-MANNO-2-OCTULOSONIC ACID DERIVATIVES, PHARMACEUTICAL COMPOSITIONS AND METHOD OF USE

TECHNICAL FIELD

The invention relates to novel inhibitors of a component of gram-negative bacteria which are useful as gram-negative antibiotics and, more particularly, to inhibitors of the gram-negative bacterial enzyme, cytidine monophosphate ketodeoxyoctulosonic acid (CMP-KDO) synthetase.

BACKGROUND ART

Gram-negative bacteria possess a structural unit in their cell envelope called the outer membrane. This layer, which is not present in gram-positive bacteria, surrounds the cell wall and provides the organism with a major barrier to mammalian host defenses and to the penetration of antibiotics. The principal structural component of the outer membrane is lipopolysaccharide (LPS) and provides the major barrier function of the outer membrane.

For instance, erythromycin and vancomycin, which are active only at very high concentrations against gram-negative organisms, are about 100-fold more active against mutants with deficiencies in LPS biosynthesis. Mutants with deficiencies in the biosynthesis of certain regions of LPS are also susceptible to the lethal actions of elements of host defenses, such as lysozyme, deoxycholate and complement which are ineffective against normal gram-negative cells.

LPS itself is comprised of structural units that include a KDO oligosaccharide and a glycolipid (Lipid A), both of which have been shown to be essential to the viability of the bacterium. Thus, inhibitors of KDO and/or Lipid A biosynthesis represent targets for the discovery of novel gram-negative antibiotics.

SUMMARY OF THE INVENTION

The present invention is directed to compounds of the formula:

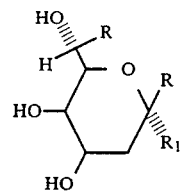

wherein R is hydrogen, sulfur, loweralkyl or allyl; $R_1$ is in an alpha orientation and is a carboxylic acid or $COR_3$ wherein $R_3$ is alkoxy or a hydroxy-substituted amine; $R_2$ is loweralkyl, azido or hydroxy-substituted alkyl; and pharmaceutically acceptable salts thereof.

As used herein, the term "allyl" refers to $CH_2-CH=CH_2$.

As used herein, the term "loweralkyl" refers to straight or branched chain alkyl radicals from 1 to 6 carbon atoms including but not limited to methyl, ethyl, n-propyl, isopropyl, n-butyl, sec-butyl, t-butyl, n-pentyl, 2,2-methylbutyl.

As used herein, the term "alkoxy" refers to straight or branched chain loweralkyl radicals containing from 1 to 6 carbon atoms and includes but is not limited to methoxy, ethoxy, n-propoxy, n-butoxy, 2-methoxy propyl.

SCHEME 1

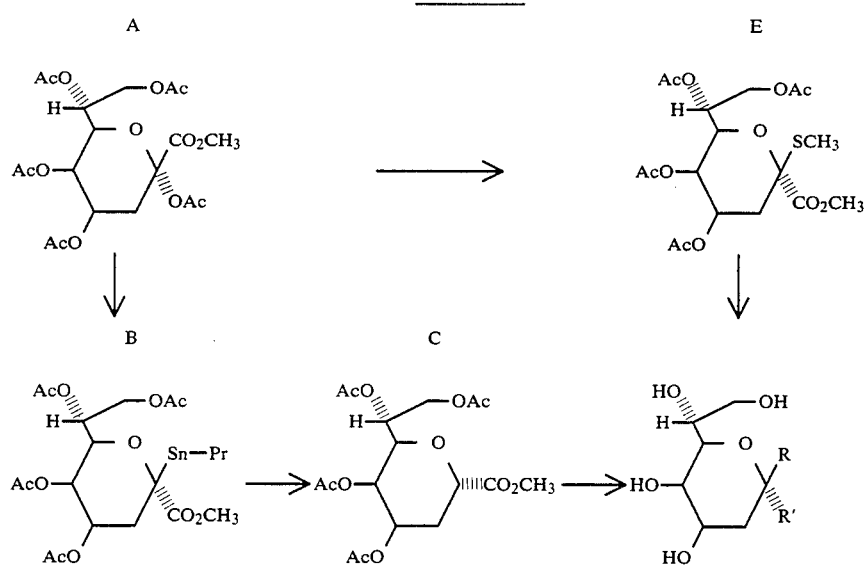

-continued

SCHEME I

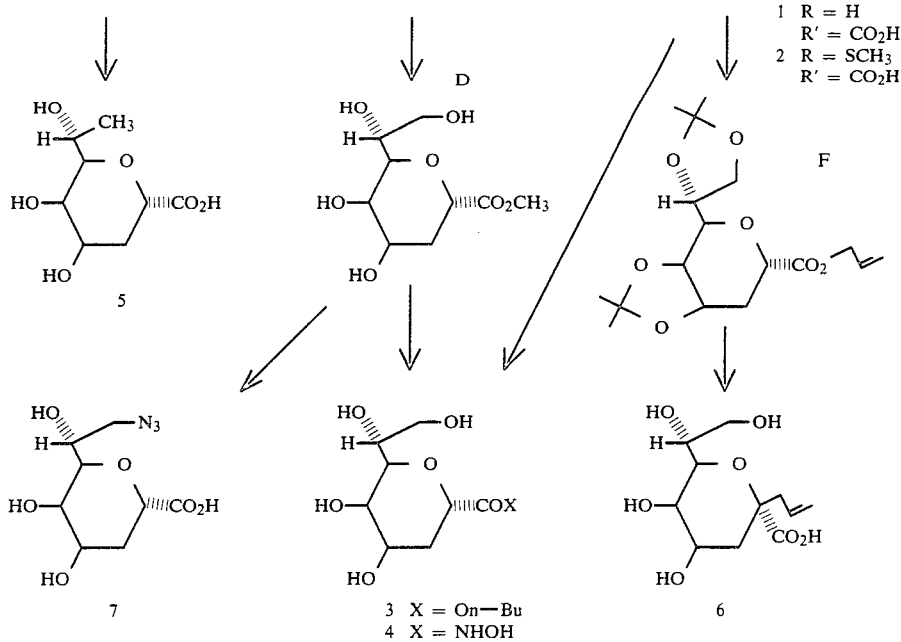

In order to illustrate the manner in which the above compounds may be prepared and the properties of the compounds, examples are set forth below, which are not meant to limit or restrict the scope of the invention in any respect.

EXAMPLE 1

α-C-(1-5-anhydro-2-deoxy-D-manno-heptopyranosyl)-carboxylate (B) Methyl (propylthio 4,5,7,8-tetra-O-acetyl-3-deoxy-βD-manno-2-octulopyranosid) onate A solution of methyl (2,4,5,7,8-penta-O-acetyl-3-deoxy-β-D-manno-2-octulopyranoson)ate (A) [Unger, F. M., Adv. Carbohydr. Chem. Biochem., 38, 323 (1981)] (22.6 g, 49 mmol) in 1-propanethiol (150 ml) was treated with zinc chloride (10 g, 73 mmol) at reflux for 2 hours. The reaction mixture was cooled, diluted with chloroform (500 ml) and washed with 5% aqueous sodium chloride. The chloroform layer was dried (magnesium sulfate) and concentrated to a syrup which was purified by silica gel chromatography. Yield 78%.

H-NMR in $CDCl_3$ [δppm from tetramethylsilane (TMS)]; 0.98~1.6 (2H, m, $CH_2$-3), 1.9~2.2 (14H, m and 4s), 2.4~2.7 (3H, m), 3.80 (3$\overline{H}$, s, $CO_2CH_3$), 3.96 (1H, q, H-6), 4.35 (2H, dd, H-8), 4.87 (1H, m, H-4), 5.20 (1H, m, H-7) 5.30 (1H, s, H-5).

C-NMR in $CDCl_3$ (δppm from TMS); 13.5 ($SCH_2CH_2CH_2CH_3$) 20.7 ($COCH_3$), 22.8 ($SCH_2CH_2CH_3$), 31.1 (C-3), 32.6 ($S\overline{C}H_2CH_2CH_3$), 52.9 ($CO_2\overline{C}H_3$), 62.4 (C-8), 64.0, 67.3, 67.$\overline{9}$, 72.0 (C-4, 5, 6, 7), 84.0 ($\overline{C}$-2), 168.7, 169.6, 169.8, 170.5, 170.6 ($\underline{C}$O).

MS (m/z) 478 (M+).

Anal. calcd. for C: 50.20, H: 6.32, S: 6.70. Found C: 49.86, H: 6.17, S: 6.60

(C) Methyl α-C-(3,4,6,7-tetra-O-acetyl-1,5-anhydro-2-deoxy-D-manno-heptopyranosyl)-carboxylate To a solution of B (3.5 g; 7.3 mmol) in ethanol (150 ml) was added Raney nickel (20 g, Grade #28) and the mixture stirred for 30 minutes at reflux. The cooled mixture was filtered, concentrated to a syrup in vacuo and purified by silica gel chromatography. Yield 46%.

H-NMR in $CDCl_3$ (δ ppm from TMS); 4.28 (2H, m, H-1 and H-7), 4.44 (1H, q, H-7), 4.67 (1H, d, H-5), 4.96 (1H, m, H-3), 5.08 (1H, m, H-6), 5.32 (1H, s, H-4).

C-NMR in $CDCl_3$ (δ ppm from TMS); 20.6 (CO$\underline{C}$H$_3$), 26.2 (C-2), 52.3 ($\underline{C}O_2CH_3$), 62.5 (C-7), 64.9, 66.7,$^-$68.0 (C-3,4,6), 70.5 (C-1), $\overline{72}$.2 (C-5) 169.7, 169.8, 170.3, 170.9 (CO).

MS (m/z) 345 (M-OAc)[30]

Anal. calcd. for C: 50.49, H: 5.98. Found C: 50.36, H: 5.97

(1) α-C-(1,5-Anhydro-2-deoxy-D-manno-heptopyranosyl)-carboxylate

Compound C (0.64 g, 1.6 mmol) was dissolved in methanol (25 ml) and treated with 5% aqueous sodium bicarbonate (6 ml) for 68 hours at room temperature. Neutralization with ion-exchange (H+) resin, filtration and evaporation gave the methyl ester D. Yield 81%.

The ester (D) (0.3 g, 1.3 mmol) was dissolved in water (20 ml) and treated with triethylamine (4 ml) at room temperature for 24 hours. The solution was neutralized with ion-exchange (H+) resin and evaporated in the presence of ammonia to give the ammonium salt of the acid (1) which was purified by silica gel chromatography. Yield 28%.

H-NMR in $D_2O$ ppm from sodium 3-trimethylsilyl-propronate-2,2,3,3-d4 (TSP)]: 2.03 (1H, m, H-2a: $J_{1,2a}=6.4$, $J_{2a,2e}=12.5$, $J_{2a,3}=4.1$ Hz), 2.23 (1H, m, H-2e: $J_{1,2e}=1.1$, $J_{2e,3}=5.4$ Hz), 3.55 (1H, d, H-5:

$J_{5,6}=8.1$ Hz), 3.71~3.85 (4H, m, H-3,6,7,7'), 3.99 (1H, d, H-4: $J_{3,4}=2.7$ Hz), 4.35 (1H, d, H-1).

C-NMR in $D_2O$ (δ ppm from TSP); 29.0 (C-2), 64.5 (C-7), 66.9 (C-4), 67.4 (C-6), 69.7 (C-3), 74.3 (C-1), 74.7 (C-5), 178.9 (CO).

MS (m/z) 221 (M-1)$^-$; FAB

Anal. calcd. for C: 38.23, H: 7.35, N, 5.58. Found C: 38.31, H: 6.99, N: 5.48.

EXAMPLE 2

Methylthio 3-deoxy-β-D-manno-2-octulopyranosidonic acid (E) Methyl (methylthio-4,5,7,8-tetra-O-acetyl-3-deoxy-β-D-manno-2-octulopyranosid)onate A solution of compound A (0.5 g, 1.1 mmol) in methanethiol (15 ml) was treated with zinc chloride (0.38 g, 2.8 mmol) at reflux for 7 hours. The reaction mixture was diluted with methylene chloride (50 ml), washed with 5% sodium chloride, dried and concentrated to a syrup. The product was purified by silica gel chromatography. Yield 80%.

H-NMR in $CDCl_3$ (δppm from TMS); 1.99, 2.01, 2.11, 2.13 (12H, 4s, $COCH_3$), 2.1 (1H, m, H-3a), 2.15 (3H, s, $SCH_3$), 2.5 (1H, m, H-3e), 3.8 (3H, s, $CO_2CH_3$), 3.94 (1H, m, H-6), 4.33 (1H, dd, H-8), 4.40 (1H, dd, H-8), 4.9 (1H, m, H-4), 5.2 (1H, m, H-7), 5.31 (1H, m, H-5).

C-NMR in $CDCl_3$ (δppm from TMS); 11.8 ($SCH_3$), 20.6 ($COCH_3$), 32.3 (C-3), 52.9 ($CO_2CH_3$), 62.3 (C-8), 64.0, 67.3, 67.9, 71.9 (C-4,5,6,7), 83.3 (C-2), 168.2, 169.6, 169.8, 170.4, 170.6 (CO).

MS (m/z) 450 (M+)

(2) Methylthio 3-deoxy-β-D-manno-2-octulopyranosidonic acid

Compound E (0.29 g, 0.64 mmol was dissolved in 0.1 M potassium hydroxide and the reaction stirred at room temperature for 20 hours. The solution was neutralized with ion-exchange (H+) resin and evaporated in the presence of ammonia to give the ammonium salt of the acid (2) which was purified by silica gel chromatography. Yield 73%.

H-NMR in $D_2O$ (δ ppm from TSP); 1.88 (1H, m H-3a; $J_{3a,3e}=12.0$, $J_{3a,4}=12.4$ Hz), 2.12 (3H, s, $SCH_3$), 2.48 (1H, m, H-3e; $J_{3e,4}=4.8$ Hz), 3.51 (1H, m, H-6; $J_{6,7}=9.0$ Hz), 3.73 (1H, m, H-8'; $J_{8,8'}=8.0$ Hz), 3.76 (1H, m, H-4), ~3.9 (2H, m, H-7,-8), 3.98 (1H, m, H-5; $J_{4,5}=3.0$ Hz).

C-NMR in $D_2O$ (δ ppm from TSP); 12.0 ($SCH_3$), 35.2 (C-3), 64.6 (C-8), 65.8 (C-5), 67.9 (C-7), 69.3 (C-4), 75.5 (C-2), 86.0 (C-2), 174.6 (C-1; $^J1$, H3a=7.1 Hz).

MS (m/z) 286 (M+H)$^+$; FAB

EXAMPLE 3 n-Butyl α-C-(1,5-anhydro-2-deoxy-D-manno-heptopyranosyl)-carboxylate

The triethylammonium salt of 1 (0.44 g, 1.4 mmol) was suspended in n-butanol (20 ml) and stirred at room temperature in the presence of dry ion exchange (H+) resin (4 g, Dowex 50W-X12) for 4 days. The reaction mixture was filtered and the solvent was removed by evaporation. The residue was reconstituted in water (5 ml) and the solution was lyophilized. Yield 59%.

H-NMR in $D_2O$ (δ ppm from TSP); 0.91 (3H, t, $CH_2CH_2CH_2CH_3$), 1.38 (2H, m, $CH_2CH_2CH_2CH_3$), 1.67 (2H, m, $CH_2CH_2CH_2CH_3$), 2.10 (1H, m, H-2a; $J_{1,2a}=6.2$, $J_{2a,2e}=12.5$, $J_{2a,3}=14.0$ Hz), 2.23 (1H, m, H-2e; $J_{1,2e}=1.0$, $J_{2e,3}=5.2$ Hz), 3.52 (1H, d, H-5; $J_{5,6}=8.7$ Hz), 3.73~3.90 (4H, m, H-3,6,7,7'), 4.0 (1H, d, H-4; $J_{3,4}=3.0$ Hz), 4.23 (2H, t, $CH_2CH_2CH_2CH_3$), 4.67 (1H, d, H-1).

C-NMR in $D_2O$ (δ ppm from TSP); 13.0 ($CH_2CH_2CH_2CH_3$), 18.7 ($CH_2CH_2CH_2CH_3$), 27.6 ($CH_2CH_2CH_2CH_3$), 29.9 (C-2), 63.7 (C-7), 66.3 (C-4), 66.4 ($CH_2CH_2CH_2CH_3$), 69.4 (C-6), 72.7 (C-1), 75.0 (C-5), 173.6 (CO).

Anal calcd. for C: 51: 79, H: 7.97. Found C: 51.22, H: 7.91

EXAMPLE 4

α-C-(1,5-Anhydro-2-deoxy-D-manno-heptopyranosyl)-hydroxamate

To a cold solution of the ester (D) (0.61 g, 2.6 mmol) in dry methanol (4 ml) was added hydroxylamine (2.8 mmol; prepared by the procedure of S. R. Sandler and W. Karo, "Organic Functional Group Preparations", Vol. 3, Academic Press, N.Y., 1972) in 1 ml dry methanol. Potassium hydroxide (170 mg) was added and the mixture was stirred at room temperature for 2 days. The solution was neutralized with ion-exchange (H+) resin and evaporated to a residue. The latter was purified by silica gel chromatography and 4 was isolated as the ammonium salt. Yield 40%. Product gives a positive reaction for a hydroxamic acid with acidic ferric chloride reagent.

H-NMR in $D_2O$ (δ ppm from TSP); 2.03 (1H, m, H-2a; $J_{1,2a}=6.0$, $J_{2a,2e}=12.9$, $J_{2a,3}=14.4$ Hz), 2.22 (1H, dd, H-2e; $J_{2e,3}=5.1$ Hz), 3.47 (1H, d, H-5; $J_{5,6}=9.0$ Hz), 3.73~3.92 (4H, m, H-3,6,7,7'), 4.0 (1H, d, H-4; $J_{3,4}=2.4$ Hz), 4.65 (1H, d, H-1).

C-NMR in $D_2O$ (δ ppm from TSP); 26.6 (C-2), 63.5 (C-7), 66.4 (C-4, C-6), 69.1 (C-3), 72.8 (C-1), 74.7 (C-5), 169.9 (CO).

MS (m/z) 236 (M-$NH_4$)$^-$; FAB

EXAMPLE 5

α-C-(1,5 Anhydro-2,7-dideoxy-D-manno-heptopyranosyl)-carboxylate

A solution of B (2.5 g, 8.1 mmol) in dry pyridine (100 ml) was treated with triphenylphosphine (4.2 g, 16 mmol) and carbon tetrabromide (5.4 g, 16 mmol) at 0° C. for 15 minutes and then at 50° C. for 1 hour. The solvents were evaporated to leave a residue which was taken up in water (10 ml) and extracted 3 times with ethyl acetate (200 ml each). The ethylacetate extracts were combined and evaporated to a residue which was dissolved in acetonitrile (200 ml) and washed exhaustively with n-hexane. The acetonitrile phase was evaporated and the residue purified by silica gel chromatography to provide the 7-bromo-7-deoxy analog.

The 7-bromo compound (0.90 g, 2.4 mmol) was dissolved in methanol (100 ml) and treated with Raney nickel (6 g, Grade #28) in the presence of sodium acetate (330 mg) and 3 atm. of hydrogen for 5 hours at room temperature. The mixture was then heated at 60° C. for 17 hours, filtered, and the solvents removed by evaporation. The residue was dissolved in a mixture of methanol (30 ml) and water (15 ml) and the pH adjusted to 13 with 12 M sodium hydroxide. After 15 minutes at room temperature the solution was neutralized with ion-exchange (H+) resin and lyophilized in the presence of ammonia to give the ammonium salt of the 8-deoxy acid (5). The latter was purified by silica gel chromatography. Yield 13%.

H-NMR in D$_2$O (δppm from TSP); 1.31 (3H, d, 7-CH$_3$; J$_{6,7}$=6.3 Hz), 2.03 (1H, m, H-2a; J$_{1,2a}$=6.0, J$_{2a,2e}$=12.3, J$_{2a,3}$=14.1 Hz), 2.18 (1H, m, H-2e; J$_{2e,3}$=5.1 Hz), 3.49 (1H, d, H-5; J$_{5,6}$=7.5 Hz), 3.74 (1H, m, H-3; J$_{3,4}$=2.7 Hz), 3.92 (1H, m, H-6), 4.02 (1H, d, H-4), 4.36 (1H, d, H-1).

C-NMR in D$_2$O (δ ppm from TSP); 19.9 (C-7), 29.1 (C-2), 66.5 (C-4), 67.3 (C-3,6), 74.7 (C-1), 78.0 (C-5), 178.8 (CO).

MS (m/z) 207 (M-NH$_3$)$^+$; FAB

EXAMPLE 6

α-C-(1-Allyl-1,5-anhydro-2-deoxy-D-manno-heptopyranosyl)-carboxylate (F) Allyl β-C-(1,5-anhydro-2-deoxy-3,4:6,7-diisopropylidene-D-manno-heptopyranosyl)-carboxylate The triethylammonium salt of compound 1 (1.7 g, 5.3 mmol) was dissolved in dry allyl alcohol (25 ml) and heated at 50° C. for 18 hours in the presence of ion-exchange (H$^+$) resin (5 g - dry). The solvent was evaporated and the residual mixture reconstituted in acetone (150 ml - dry). After 3 hours at 50° C. the mixture was filtered and the solvent removed by evaporation. The residue was purified by silica gel chromatography. Yield 15%.

H-NMR in CDCl$_3$ (δ ppm from TMS); 1.36, 1.38, 1.44, 1.48 (12H, 4s, CCH$_3$), 2.02 (1H, m, H-2a; J$_{1,2a}$=8.7, J$_{2e,2a}$=13.9, J$_{2a,3}$=8.0 Hz), 2.18 (1H, m, H2e; J$_{1,2e}$=4.4, J$_{2e,3}$=5.7 Hz), 3.55 (1H, dd, H-5; J$_{4,5}$=2.0, J$_{5,6}$=6.0 Hz), 4.09 (1H, dd, H-1), 4.11 (2H, m, H-7), 4.20 (1H, m, H-4), 4.34~4.42 (2H, m, H-4,-6), 4.63~4.68(2H, m, CH$_2$CH=CH$_2$), 5.23~5.37 (2H, m, CH$_2$CH=CH$_2$), 5.92 (1H, m, CH$_2$CH=CH$_2$).

C-NMR in CDCl$_3$ (δ ppm from TMS); 25.4, 25.9, 27.0, 27.4 (C-CH$_3$), 30.5 (C-2), 65.6 (C-7), 66.9 (CH$_2$CH=CH$_2$), 71.1, 71.3, 72.4, 74.3, 75.6 (C-1,3,4,5,6) 109.2, 109.6 (CCH$_3$), 118.6 (CH$_2$CH=CH$_2$), 131.7 (CH$_2$CH=CH$_2$), 174.3 (CO).

MS (m/z) 342 (M)$^+$ (6) α-C-(1-Allyl-1,5-anhydro-2-deoxy-D-manno-heptopyranosyl)-carboxylate Compound F (0.17 g, 0.50 mmol) in dry tetrahydrofuran (3 ml) was cooled to −78° C. and treated with cold (−78° C.) lithiated hexamethyldisilazane reagent [1.1 mmol in 5 ml tetrahydrofuran; prepared by the procedure of R. E. Ireland, et al., *J. Amer. Chem. Soc.*, 98, 2868 (1976)]. After 5 minutes trimethylsilyl chloride (0.16 ml, 1.3 mmol) was added and the −78° C. cold bath was removed. The reaction was quenched with methanol (0.5 ml) after 1 hour and, after 2 hours, conc. aqueous ammonia (0.2 ml) was added. The solvents were removed by evaporation and the product purified by silica gel chromatography. Yield 41%.

The latter product (0.031 g, 0.11 mmol) was dissolved in a mixture of tetrahydrofuran (2 ml) and aqueous 2 M trifluoroacetic acid (8 ml). The solvents were removed by evaporation after 2 hours and the product (6) purified by silica gel chromatography and isolated as the ammonium salt. Yield 33%.

H-NMR in D$_2$O (δppm from TSP); 1.78 (1H, t, H-2a; J$_{2a,2e}$=12.0, J$_{2a,3}$=12.5), 1.94 (1H, dd, H-2e; J$_{2e,3}$=5.1 Hz), 2.48 and 2.83 (1H each, q, CH$_2$CH=CH$_2$), 3.58 (1H, d, H-5; J$_{5,6}$=6.9 Hz), 3.62~3.90 (3H, m, H-3,7,7'), 3.95 (1H, d, H-4; J$_{3,4}$=3.0 Hz), 4.05 (1H, m, H-6), 5.12 (2H, m, CH$_2$CH=CH$_2$), 5.66 (1H, m, CH$_2$CH=CH$_2$).

C-NMR in D$_2$O (δ ppm from TSP); 34.5 (C-2), 36.2 (CH$_2$CH=CH ), 63.9 (C-7), 67.0 (C-4), 67.3 (C-6), 70.6 (C-3), 72.5 (C-5), 81.5 (C-1), 118.4 (CH$_2$CH=CH$_2$) 133.8 (CH$_2$CH=CH$_2$), 180.5 (CO).

The stereochemistry of the anomeric center was assigned by a two-dimensional Nuclear Overhauser Effect technique.

MS (m/z) 261 (m-NH$_4$)$^-$; FAB

EXAMPLE 7

α-C-(1,5-Anhydro-7-azido-2,7-dideoxy-D-manno-heptopyranosyl)-carboxylate

To a solution of the ester (D) (0.74 g, 3.2 mmol) in dry dimethylformamide (20 ml) was added carbon tetrachloride (0.76 g, 4.9 mmol), triphenylphosphine (1.1 g, 4.3 mmol), and sodium azide (0.64 g, 9.8 mmol). The mixture was stirred at room temperature for 20 hours. Solvents were removed by evaporation and the crude product was purified by silica gel chromatography to provide the ammonium salt of 7. Yield 35%.

H-NMR in D$_2$O (δppm from TSP); 1.92 (1H, m, H-2a; J$_{1,2a}$=9.0, J$_{2a,2e}$=12.0, J$_{2a,3}$=13.2), 2.05 (1H, dd, H-2e; J$_{2e,3}$=5.4 Hz), 3.33 (1H, dd, H-7, J$_{7,7'}$=13.5 Hz), 3.47 (1H, d, H-5; J$_{5,6}$=9.0 Hz), 3.73 (1H, dd, H-7'), 3.66 (1H, m, H-3; J$_{3,4}$=2.8 Hz), 3.85 (1H, d, H-4), 4.45 (1H, d, H-1).

C-NMR in D$_2$O (δppm from TSP); 27.9 (C-2), 54.0 (C-7), 66.4 (C-4), 66.5 (C-6), 68.4 (C-3), 72.9 (C-1), 74.9 (C-5), 175.7 (CO).

MS (m/z) 265 (M+H)$^+$; FAB

TABLE I

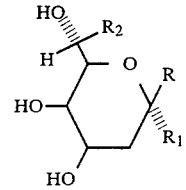

| Example | R | R$_1$ | R$_2$ | I$_{50}$ (mM) |
|---|---|---|---|---|
| 1 | H | COOH | CH$_2$OH | 0.023 |
| 2 | SCH$_3$ | COOH | CH$_2$OH | 3.2 |
| 3 | H | CO$_2$(CH$_2$)$_3$CH$_3$ | CH$_2$OH | 1.3 |
| 4 | H | CONHOH | CH$_2$OH | 0.10 |
| 5 | H | COOH | CH$_3$ | 0.008 |
| 6 | CH$_2$—CH=CH$_2$ | COOH | CH$_2$OH | 1.2 |
| 7 | H | COOH | CH$_2$N$_3$ | 0.14 |

The novel compounds of the present invention are potent inhibitors of the enzyme CMP-KDO synthetase and, accordingly, effective, gram-negative antibacterial agents. The biological properties of the compounds are summarized in Table I.

The inhibition of CMP-KDO synthetase activity was measured in reaction mixtures buffered at pH 9.5 containing: 2 mM KDO, 5 mM magnesium cytidine triphosphate, and inorganic pyrophosphatase. The pyrophosphate generated during the course of enzyme reaction was cleaved by the pyrophosphatase to inorganic orthophosphate, the level of which was measured colorimetrically. The efficacy of the inhibitors was calculated from the extent they inhibited phosphate production compared to a control which did not contain inhibitor. Potency was assessed by determining the level of inhibitor required to inhibit the enzyme reaction by 50% under the conditions of the assay described above ($I_{50}$). A potent inhibitor is defined as one having an $I_{50}$ of 4 mM or less.

The compounds of the present invention can be used in the form of suitable salts such as, for example, sodium, potassium, calcium, magnesium, aluminum, ammonium, ceric, chromic, cobaltic, cupric, ferric, silver, zinc, and organic base salts.

Total daily dose administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable preparation, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

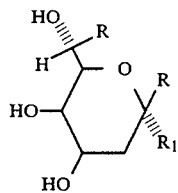

wherein R is hydrogen, methylthio, alkyl or loweralkyl; $R_1$ is in an alpha orientation and is a carboxylic acid for $COR_3$ wherein $R_3$ is alkoxy or —NHOH; $R_2$ is loweralkyl, azido or hydroxy-substituted alkyl; and pharmaceutically acceptable salts thereof.

2. A compound as defined in claim 1 wherein R is hydrogen, $R_1$ is —$CO_2H$ and $R_2$ is —$CH_2OH$ or $CH_3$.

3. A composition having antibacterial activity in pharmaceutical dosage form containing a diluent and a compound as defined in claim 1.

4. A method of treating bacterial infection in a patient comprising administering to a patient in need of such treatment a therapeutically effective amount of a compound as defined in claim 1.

* * * * *

UNITED STATES PATENT AND TRADEMARK OFFICE
CERTIFICATE OF CORRECTION

PATENT NO. : 4,613,589

DATED : September 23, 1986

INVENTOR(S) : William Rosenbrook, Paul A. Lartey; David A. Riley

It is certified that error appears in the above—identified patent and that said Letters Patent is hereby corrected as shown below:

Claim 1, lines 30-38, delete structure and insert structure as follows:

-- 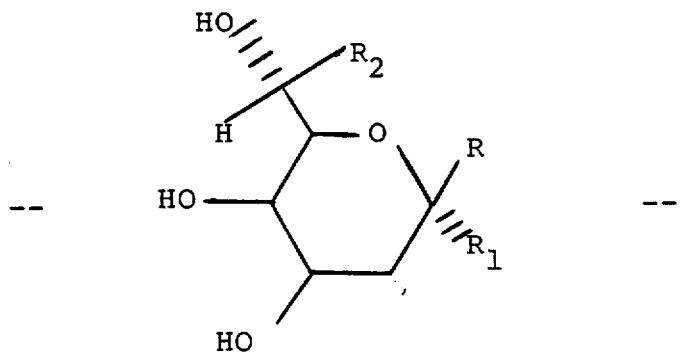 --

Signed and Sealed this

Sixth Day of January, 1987

*Attest:*

DONALD J. QUIGG

*Attesting Officer*  *Commissioner of Patents and Trademarks*